US009328037B2

(12) United States Patent
Riley et al.

(10) Patent No.: US 9,328,037 B2
(45) Date of Patent: May 3, 2016

(54) BENZENE ALKYLATION USING ACIDIC IONIC LIQUIDS

(71) Applicants: UOP LLC, Des Plaines, IL (US); Boreskov Institute of Catalysis, Novosibirsk (RU)

(72) Inventors: Mark G. Riley, Hinsdale, IL (US); Alakananda Bhattacharyya, Glen Ellyn, IL (US); Nikolay Yu. Adonin, Novosibirsk (RU); Mariya N. Timofeeva, Novosibirsk (RU); Sergey A. Prikhodko, Novosibirsk (RU); Bair S. Bal'zhinimaev, Novosibirsk (RU)

(73) Assignees: UOP LLC, Des Plaines, IL (US); BORESKOV INSTITUTE OF CATALYSIS, Novosibirsk (RU)

( * ) Notice: Subject to any disclaimer, the term of this patent is extended or adjusted under 35 U.S.C. 154(b) by 187 days.

(21) Appl. No.: 14/327,185

(22) Filed: Jul. 9, 2014

(65) Prior Publication Data

US 2016/0009612 A1    Jan. 14, 2016

(51) Int. Cl.
| | |
|---|---|
| C07C 2/68 | (2006.01) |
| C07C 2/70 | (2006.01) |
| C07C 5/05 | (2006.01) |
| C07C 5/08 | (2006.01) |
| C07C 5/09 | (2006.01) |
| C07C 5/327 | (2006.01) |
| C07C 2/66 | (2006.01) |

(52) U.S. Cl.
CPC ............... *C07C 2/66* (2013.01); *C07C 2527/14* (2013.01); *C07C 2527/24* (2013.01)

(58) Field of Classification Search
USPC ......... 585/323, 259, 455, 456, 457, 459, 461, 585/462, 463, 654, 831
See application file for complete search history.

(56) References Cited

U.S. PATENT DOCUMENTS

| | | | |
|---|---|---|---|
| 5,196,574 A | 3/1993 | Kocal | |
| 5,276,231 A * | 1/1994 | Kocal | .................... C07C 15/107 585/259 |
| 5,824,832 A | 10/1998 | Sherif et al. | |

(Continued)

FOREIGN PATENT DOCUMENTS

| | | |
|---|---|---|
| CN | 1785940 A | 6/2006 |
| CN | 102666444 A | 9/2012 |

(Continued)

OTHER PUBLICATIONS

Qiao et al., "Activity and stability investigation of [BMIM][AlCl4] ionic liquid as catalyst for alkylation . . . ," Applied Catalysis A: General (2004), 276(1-2), 61-66.

(Continued)

*Primary Examiner* — Thuan D Dang

(57) ABSTRACT

A process for making linear alkyl aromatics is described. The process involves preparing the paraffin feed by dehydrogenating normal paraffins, selectively hydrogenating any diolefins, and adsorbing any aromatics to form an olefin feed. The olefin feed is contacted with an aromatic feed in the presence of an ionic liquid catalyst to form a mixture of alkylated aromatics. The ionic liquid catalyst is separated from the mixture of alkylated aromatics by gravity, and any ionic liquid retained in the alkylated aromatics is removed by adsorption or extraction. The mixture of alkylated aromatics is then separated into monoalkylated aromatics and dialkylated aromatics.

13 Claims, 1 Drawing Sheet

(56) References Cited

U.S. PATENT DOCUMENTS

| | | | |
|---|---|---|---|
| 5,994,602 | A | 11/1999 | Abdul-Sada et al. |
| 7,256,152 | B2 | 8/2007 | Olivier-Bourbigou et al. |
| 7,314,962 | B2 | 1/2008 | Harmer et al. |
| 8,105,481 | B2 * | 1/2012 | Driver ............ C07C 2/60 208/262.1 |
| 8,524,965 | B2 | 9/2013 | Campbell et al. |
| 2007/0100184 | A1 | 5/2007 | Harmer et al. |

FOREIGN PATENT DOCUMENTS

| | | |
|---|---|---|
| EP | 2520558 A1 | 11/2012 |
| WO | WO 95/21871 A1 | 8/1995 |

OTHER PUBLICATIONS

Qiao et al., "Recycling and activity recovery of Chloroaluminate ionic liquid as catalyst for alkylation . . . ," Chinese Journal of Process Engineering (2006), 6(2), 302-307.

Sun et al., "[BMIM]Cl/[FeCl3] Ionic Liquid as Catalyst for Alkylation of Benzene with 1-Octadecene," Chinese Journal of Chemical Engineering (2006), 14(3), 289-293.

Zhu et al., "Effects of chloroaluminate ionic liquid on alkylation of benzene with mixture . . . ," Bulletin of the Catalysis Society of India (2007), vol. 6, 83-89.

Dai, Jifeng, "Investigation of catalytic reactions in novel ionic liquids," Thesis for Ph.D degree—Dublin City University (2003), 1-28.

Shi et al., "Alkylation of benzene and 1-dodecene catalyzed by Et3NHCl-xAlCl3 ionic liquids", Chemical Reaction Engineering and Technology (2007), 23(2), 120-125 104.

Xin et al., "Alkylation of benzene with 1-dodecene in ionic liquids [Rmim]+Al2Cl6X—(R=butyl, octyl and dodecyl). . . ", Applied Catalysis A: General (2005), 292(1-2), 354-361.

Qi et al., "Alkylation mechanism of benzene with 1-dodecene catalyzed by Et 3NHCl-AlCl3," Science China Chemistry (2010), 53(5), 1102-1107.

Qi et al., "Friedel-Crafts alkylation of benzene with 1-hexadecene in ionic liquids prepared in situ", Petroleum Science and Technology (2009), 27(16), 1800-1809.

Sun et al., "Alkylation of Benzene with Hexene Catalyzed by Ionic Liquid", Petrochemical Technology (2003), 32(7), 570-572.

Wang et al., "Akylation of bibenzyl with dodecene-1 catalyzed by ionic liquids at room temperature," Acta Petrolei Sinica (Petroleum Processing Section)(2006), 22(4), 39-43.

* cited by examiner

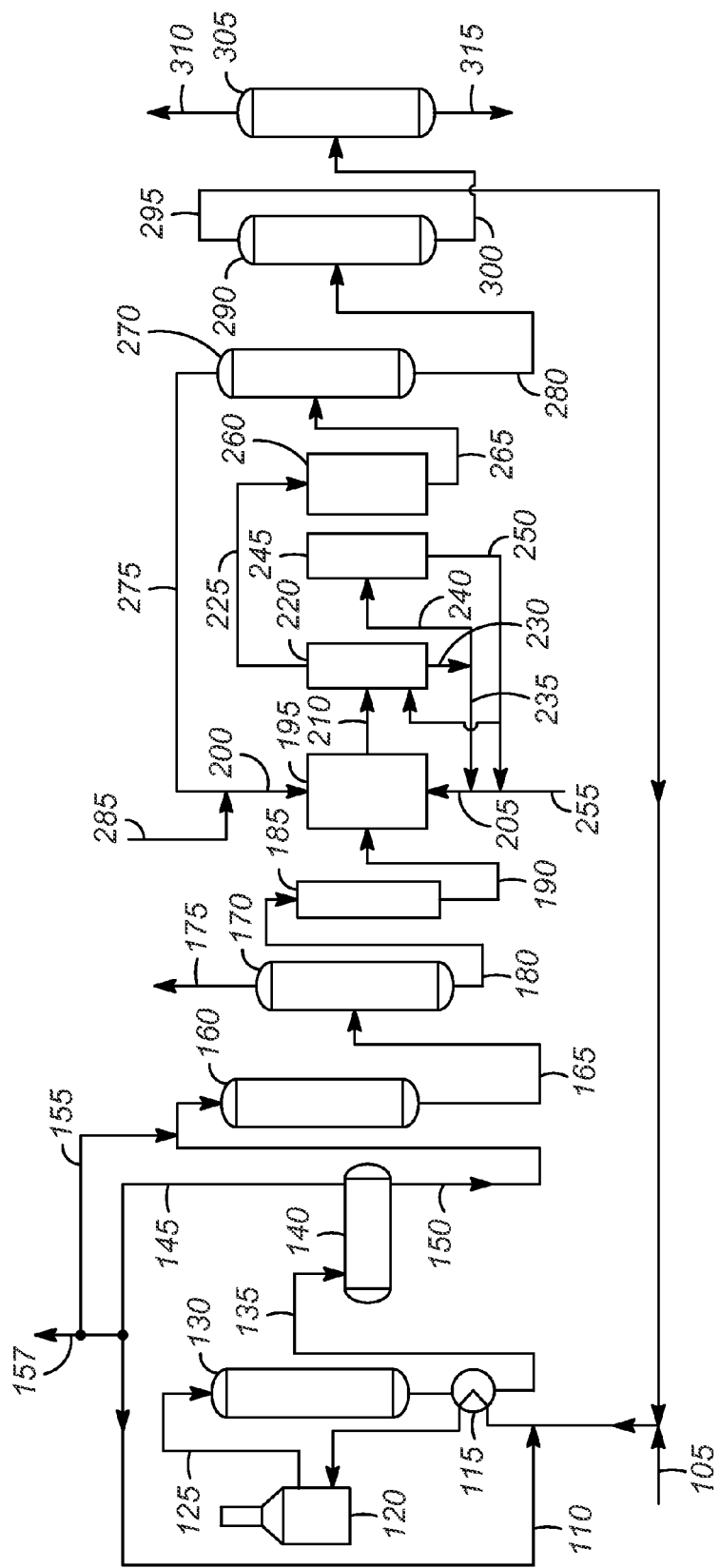

BENZENE ALKYLATION USING ACIDIC IONIC LIQUIDS

BACKGROUND OF THE INVENTION

Linear alkylbenzenes (LAB) are compounds that have significant commercial importance. Linear alkylbenzene sulfonate (LAS) compounds made by sulfonation of linear alkylbenzene are used in the manufacture of detergents and other products. Because linear alkylbenzenes are more easily biodegradable than branched alkylbenzenes, linear alkylbenzenes have essentially replaced branched alkylbenzenes in detergents and other products. In particular, linear alkylbenzenes with long alkyl chains, such as chains having about 10 to about 14 carbons, are commonly used. However, linear alkylbenzenes with longer chains and with shorter chains also are commercially important.

Linear alkylbenzenes often are made by alkylation of benzene with olefins. Positional isomers, such as 2-phenyl, 3-phenyl, 4-phenyl, 5-phenyl, and the like, result from this alkylation of benzene with long chain olefins. The distribution of the phenyl along the alkyl chain produces different products.

Historically, linear alkylbenzenes have been manufactured commercially using Friedel-Crafts condensation employing catalysts such as aluminum chloride, or by using strong acid catalysts such as hydrogen fluoride, for example, to alkylate benzene with olefins. Currently, about two thirds of the LAB used for detergent is manufactured using the HF process. However, hydrogen fluoride is hazardous and corrosive, and its use in industrial processes requires a variety of environmental controls.

There has been significant effort in developing alternatives to the HF alkylation process, particularly in the area of motor fuels alkylation. The formulation of detergent products has been built around a particular isomeric distribution of phenyl alkanes produced by HF alkylation. Therefore, it would be desirable to produce a product having a distribution of phenyl alkanes similar to that of HF alkylation and within the commercial range specified based on that distribution.

There exists a need for additional methods for making linear alkylaromatics.

SUMMARY OF THE INVENTION

One aspect of the invention is a process for making linear alkyl aromatics. In one embodiment, the process includes dehydrogenating normal paraffins in a dehydrogenation zone to form a stream comprising olefins. Diolefins in the stream comprising olefins are selectively hydrogenated in a selective hydrogenation zone to form a stream comprising normal olefins. Aromatics from the stream comprising normal olefins are adsorbed in an aromatics adsorption unit to form a stream comprising olefins having a lower aromatic content. An aromatic feed and the stream comprising olefins having the lower aromatic content are contacted in the presence of an ionic liquid catalyst in an alkylation reaction zone under alkylating conditions to form a product mixture comprising a mixture of alkylated aromatics comprising monoalkylated aromatics and dialkylated aromatics. The mixture of alkylated aromatics comprising greater than 90% linear alkylated aromatics. The volume ratio of ionic liquid catalyst to hydrocarbon is in the range of 0.05:1 to 2.0:1, and the hydrocarbon comprising the aromatic feed and the alkylating agent, and wherein a molar ratio of the aromatic feed to the olefin is in a range of 4:1 to 8:1. The ionic liquid catalyst is separated from the product mixture by gravity into an ionic liquid catalyst stream and a stream of the product mixture. Any retained ionic liquid catalyst is removed from the stream of the product mixture by adsorption or extraction. The stream of the product mixture is separated into a stream comprising the monoalkylated aromatics and a stream comprising the dialkylated aromatics.

BRIEF DESCRIPTION OF THE DRAWING

The FIGURE illustrates one embodiment of a process for making linear alkyl aromatics according to the present invention.

DETAILED DESCRIPTION OF THE INVENTION

Integrated processes for producing LABs using ionic liquid catalysts have been developed. One example of an integrated process is shown in FIG. 1 which includes a dehydrogenation process, followed by a selective catalytic hydrogenation process, aromatics separation process, and an alkylation process.

As illustrated in FIG. 1, the hydrocarbon feed 105 is mixed with hydrogen 110 and preheated in a heat exchanger 115. The preheated feed is sent to a charge heater 120 where it is heated to the desired temperature. The heated feed 125 is then sent to the dehydrogenation reaction zone 130.

In the dehydrogenation process, the hydrocarbon feed 105 typically includes hydrocarbons having 6 to 30 carbon atoms including paraffins, and isoparaffins, with small amounts (e.g., less than 5%, or less than about 2%) of alkylaromatics, naphthenes, and olefins. In some embodiments, the feed contains hydrocarbons having 8 to 18, or 9 to 14 carbon atoms. The feed will typically include only a small portion of this range (e.g., 2, 3, or 4 carbon numbers, and they would typically be consecutive carbon numbers), because the rate of reaction is carbon number dependent. At a given temperature, higher carbon number paraffins will react more readily to produce higher conversion than lower carbon numbers. A suitable feed of dehydrogenatable hydrocarbons will often contain light hydrocarbons (i.e., those having less carbon atoms than the primary feed components) which, for the purpose of reaction, serve as contaminants In most cases, olefins are excluded from the dehydrogenation zone recycle in order to avoid the formation of dienes which produce unwanted by-products in many of the olefin conversion processes.

The hydrocarbon feed 105 is typically mixed with hydrogen 110 under pressure before it reaches the dehydrogenation reaction zone 130. The mixing pressure may be slightly higher than the reactor pressure to allow for a drop in the lines between the mixer and the dehydrogenation reaction zone 130. The hydrogen 110 in the hydrocarbon feed 105 acts to suppress the formation of hydrocarbonaceous deposits on the surface of the catalyst, more typically known as coke, and can act to suppress undesirable thermal cracking. Because hydrogen is generated in the dehydrogenation reaction and comprises a portion of the dehydrogenation effluent 135, the hydrogen-rich stream 110 introduced into the dehydrogenation reaction zone 130 generally comprises recycle hydrogen derived from separation of the dehydrogenation effluent 135. Alternately, the hydrogen may be supplied from suitable sources other than the dehydrogenation effluent 135.

The hydrocarbon feed 105 and hydrogen 110 are passed through the dehydrogenation reaction zone 130.

The dehydrogenation reaction zone 130 is typically a radial flow reactor operated in the vapor phase with a very low pressure drop. Typical conditions for dehydrogenation of $C_{10}$ to $C_{13}$ hydrocarbons include an inlet temperature of 475° C., 138 kPa(g) (20 psig), and a hydrogen to hydrocarbon ratio of between 5:1 to 6:1.

Any suitable dehydrogenation catalyst may be used in the present invention. Generally, one preferred suitable catalyst comprises a Group VIII noble metal component (e.g., platinum, iridium, rhodium, and palladium), an alkali metal component, and a porous inorganic carrier material. The catalyst may also contain promoter metals which advantageously improve the performance of the catalyst.

Newer dehydrogenation catalysts can also be used in this process. For example, one such catalyst comprises a layered catalyst composition comprising an inner core, and outer layer bonded to the inner core so that the attrition loss is less than 10 wt % based on the weight of the outer layer. The outer layer is a refractory inorganic oxide. Uniformly dispersed on the outer layer are at least one platinum group metal, and a promoter metal. The inner core and the outer layer are made of different materials. A modifier metal is also dispersed on the catalyst composition. The inner core is made from alpha alumina, theta alumina, silicon carbide, metals, cordierite, zirconia, titania, and mixtures thereof. The outer refractory inorganic oxide is made from gamma alumina, delta alumina, eta alumina, theta alumina, silica/alumina, zeolites, non-zeolitic molecular sieves, titania, zirconia, and mixtures thereof. The platinum group metals include platinum, palladium, rhodium, iridium, ruthenium, osmium, and mixtures thereof. The platinum group metal is present in an amount from about 0.01 to about 5 wt % of the catalyst composition. The promoter metal includes tin, germanium, rhenium, gallium, bismuth, lead, indium, cerium, zinc, and mixtures thereof. The modifier metal includes alkali metals, alkaline earth metals, and mixtures thereof. Further discussion of two layered dehydrogenation catalysts can be found in U.S. Pat. No. 6,617,381, which is incorporated herein by reference, for example.

The dehydrogenation reaction is a highly endothermic reaction which is typically effected at low (near atmospheric) pressure conditions (e.g. about 30 kPa to about 300 kPa).

The precise dehydrogenation temperature and pressure employed in the dehydrogenation reaction zone will depend on a variety of factors, such as the composition of the paraffinic hydrocarbon feedstock, the activity of the selected catalyst, and the hydrocarbon conversion rate. Under the conditions of the reaction, the molar ratio of hydrogen to hydrocarbon in the dehydrogenation reactor is generally in the range of about 4 to about 20, or about 2 to about 10. The conversion is desirably no more than about 16% to ensure that the yield of monoolefins is high while the yields of diolefins and aromatics are reduced. The conversion is typically in the range of about 9 to about 16% for $C_{10}$ to $C_{13}$ hydrocarbons.

Dehydrogenation of paraffins follows a successive-reaction pathway in which paraffins are dehydrogenated to olefins, olefins to diolefins, and subsequently to alkylaromatics. Longer chain paraffins tend to crack with longer residence time. The LHSV is generally in the range of about 10 to about 40.

The hydrocarbon feed reacts and produces a product mixture comprising monoolefins and hydrogen. There will be some unreacted paraffins in the product mixture. The dehydrogenation effluent 135 exchanges heat with the incoming feed 105 in heat exchanger 115. The dehydrogenation effluent 135 is sent to a separator 140, where it is separated into a hydrogen gas stream 145 and a liquid stream 150. Any suitable separator 140 can be used, including but not limited to, a flash vessel.

The hydrogen gas stream 145 can be split into the hydrogen stream 110 which is recycled and mixed with the hydrocarbon feed 105, hydrogen stream 155 which can be sent to other processes, and a hydrogen rich offgas stream 160.

Liquid stream 150 comprises the monoolefins and the unreacted paraffins. Liquid stream 150 can be combined with hydrogen stream 155 and sent to a selective hydrogenation reaction zone 160 for the hydrogenation of any diolefins to monoolefins. U.S. Pat. No. 5,276,231, for instance, discloses the selective hydrogenation of diolefinic by-products from dehydrogenation.

The effluent 165 from the selective hydrogenation reactor 160 is sent to a stripper 170 where light ends 175 are removed.

The bottoms stream 180 from the stripper 170 is sent to an aromatics separation zone 185 to remove any aromatics. Suitable aromatics removal zones for this embodiment of the invention include sorptive separation zones. Sorptive separation zones include fixed bed or moving or fluidized sorbent bed systems, but the fixed bed system is preferred. The sorbent may be installed in one or more vessels and in either series or parallel flow. The flow of the feedstock containing the aromatic by-products through the sorptive separation zones is preferably performed in a parallel manner so that one or more sorption beds can be undergoing regeneration while one or more beds are removing aromatic by-products.

Suitable sorbents may be selected from materials which exhibit the primary requirement of selectivity for the aromatic by-products and which are otherwise convenient to use. Suitable sorbents include, for example, molecular sieves, silica, activated carbon activated charcoal, activated alumina, silica-alumina, clay, cellulose acetate, synthetic magnesium silicate, macroporous magnesium silicate, and/or macroporous polystyrene gel. It should be understood that the above-mentioned sorbents are not necessarily equivalent in their effectiveness. The choice of sorbent will depend on several considerations including the capacity of the sorbent to retain aromatic by-products, the selectivity of the sorbent to retain the aromatic by-products which are more detrimental to solid alkylation catalysts, and the cost of the sorbent. One example of a suitable sorbent is a molecular sieve, such as 13 X zeolite (sodium zeolite X).

Those skilled in the art are able to select the appropriate conditions for operation of the sorbent without undue experimentation. For example, a fixed bed sorptive separation zone containing 13 X zeolite may be maintained at a temperature generally from about 20° C. (68° F.) to 300° C. (572° F.), and preferably from about 100° C. (212° F.) to 200° C. (392° F.), a pressure effective to maintain the stream containing the aromatic by-products in a liquid phase at the chosen temperature, and a liquid hourly space velocity from about 1 $hr^{-1}$ to about 10 $hr^{-1}$ and preferably from about 1 $hr^{-1}$ to about 3 $hr^{-1}$. The flow of the feedstock through a fixed or moving sorption bed may be conducted in an upflow, downflow or radial-flow manner.

Although both liquid and vapor phase operations can be used in many sorptive separation processes, liquid phase operation is preferred for the sorptive separation zone because of the lower temperature requirements and because of the higher sorption yields of the aromatic by-products that can be obtained with liquid phase operation over those obtained with vapor phase operation. Therefore, the temperature and pressure of the sorptive separation are preferably selected to maintain the feedstock in a liquid phase. The resulting unsorbed stream having a reduced concentration of aromatic by-products is a desorption effluent. However, the operating conditions of a sorptive separation zone can be optimized by those skilled in the art to operate over wide ranges which are expected to include the conditions in the reaction zones of the invention and its variants. Therefore, a sorptive separation zone may be contained in a common reaction vessel with the dehydrogenation zone, the selective diolefin hydrogenation zone, or the selective alkylation zone.

The effluent 190 from the aromatics separation zone 185 is sent to the alkylation reaction zone 195. The effluent 190, which is the aliphatic feedstock used in the alkylation process, contains aliphatic mono-olefin of 6 to 30, or 8 to 18, or 9 to 14 carbon atoms per molecule. The aliphatic olefin is usually a mixture of olefins having different molecular weights. The olefin typically comprises a mixture of olefin isomers.

The effluent 190 containing the mono-olefin feed is contacted with an aromatic stream 190 along with an ionic liquid catalyst stream 205. Suitable aromatics include, but are not limited to, benzene, toluene, and xylene The molar ratio of aromatic feed to olefin is desirably in the range of 4:1 to 8:1. This ratio impacts the energy efficiency of the process because unreacted benzene must be distilled and recycled. Operating at low aromatic to olefin ratios minimizes the utility costs associated with the aromatic distillation. However, as the ratio falls below 4:1, the rate of reaction increases dramatically. Although not wishing to be bound by theory, this may be due to the decreased solubility of the ionic liquid in the hydrocarbon phase as the hydrocarbon phase becomes more paraffinic.

The ionic liquid is very active. The volume ratio of ionic liquid to hydrocarbon (including both the aromatic feed and the olefin alkylating agent) is typically in the range of 0.05:1 to 2:1, or 0.5:1 to 2:1, or 1:1 to 1.5:1. However, operating at low ratios (e.g., 0.20:1 or less) of ionic liquid makes it more difficult to manage to reaction exotherm, and makes the process more sensitive to contaminants such as water. In addition, operating at higher ratios helps to separate out the monoalkylated species, which is the desirable product, making it more difficult to further react and produce more dialkylated products.

One or more ionic liquids can be used.

The ionic liquid comprises an organic cation and an anion. Suitable organic cations include, but are not limited to:

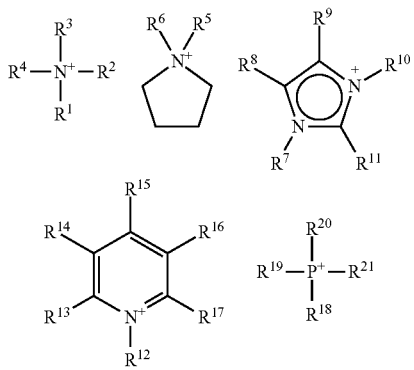

where $R^1$-$R^{21}$ are independently selected from $C_1$-$C_{20}$ hydrocarbons, $C_1$-$C_{20}$ hydrocarbon derivatives, halogens, and H, and lactamium based cations. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable. Lactamium based ionic liquids include, but are not limited to, those described in U.S. Pat. No. 8,709,236, U.S. application Ser. No. 14/271,308, entitled Synthesis of Lactam Based Ionic Liquids, filed May 6, 2014, and U.S. application Ser. No. 14/271,319, entitled Synthesis of N-Derivatized Lactam Based Ionic Liquids, filed May 6, 2014, which are incorporated by reference.

The anion can be derived from halides, sulfates, bisulfates, nitrates, sulfonates, fluoroalkanesulfonates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

Halometallates are useful, particularly chlorometallates, bromometallates, or combinations thereof. In some embodiments, the ratio of the metal in the halometallate to the cation of the ionic liquid is in a range of from 2:1 to 4:1.

Examples of suitable ionic liquids include, but are not limited to, 1-Butyl-3-methylimidazolium $AlCl_4$, 1-butyl-3-methylimidazolium $Al_2Cl_7$, 1-hexyl-3-methylimidazolium $AlCl_4$, and 1-hexyl-3-methylimidazolium $Al_2Cl_7$, and combinations thereof.

In some embodiments, an acid or acid precursor, such as HCl, 2-chlorobutane, tert-butyl chloride, and the like, is added to the ionic liquid.

The alkylation reaction conditions typically include a temperature of from about 0° C. to about 80° C., and a pressure of from about 0.1 MPa to about 5 MPa. The reaction time is typically about 10 min to about 30 min.

The contacting step may be practiced in laboratory scale experiments through full scale commercial operations. The process may be operated in batch, continuous, or semi-continuous mode. The contacting step can take place in various ways, with both concurrent and co-current flow processes being suitable. The order of addition of the reactants is not critical. For example, the reactants can be added individually, or some reactants may be combined or mixed before being combined or mixed with other reactants.

The reaction forms a mixture of alkylated products including monoalkylated products and dialkylated products. The mixture of alkylated aromatics typically includes greater than 90 wt % linear alkylated aromatics, or less than about 8 wt % dialkylated aromatics.

In some embodiments the ratio of monoalkylated aromatics to total alkylated product is greater than about 0.93, or greater than about 0.94, or greater than about 0.95, or greater than about 0.96, or greater than about 0.97, or greater than about 0.98.

In some embodiments, the selectivity for linear alkylated benzene is greater than 96%, or greater than 97%, or greater than 98%, or greater than 99%. This is much higher selectivity than with HF alkylation (typically about 93%).

The effluent 210 includes the mixture of alkylated products, the ionic liquid catalyst, and unreacted aromatics and paraffins. The effluent is sent to a gravity settler 220 where an alkylated products stream 225 (including the unreacted aromatics and paraffins) is separated from an ionic liquid catalyst stream 230. Gravity separation takes place in about 30 min to about 3 hr, or about 30 min to about 2 hr, or about 30 min to about 1 hr. Other separation devices could be used to reduce the separation time, if desired. However, with some alternate separation devices, e.g., centrifugal separators, the energy costs may increase.

All or a portion 235 of the ionic liquid catalyst stream 230 from the gravity settler 220 can be recycled to the alkylation reaction zone 195. All or a portion 240 of the ionic liquid catalyst stream 230 can be sent to regeneration zone 245 where spent ionic liquid catalyst is regenerated. The regenerated ionic liquid catalyst 250 can be recycled to the alkylation reaction zone 195 and/or the gravity settler 220.

The ionic liquid can be regenerated in a variety of ways. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. Nos. 7,651,970; 7,825,055; 7,956,002; 7,732,363, each of which is incorporated herein by reference. Another method involves contacting the ionic liquid containing the conjunct polymer with a reducing metal (e.g., Al) in the presence of an inert hydrocarbon (e.g. hexane) and heating to about 100° C. The conjunct polymer will be transferred to the hydrocarbon phase, allowing for the conjunct polymer to be removed from the ionic liquid phase. See e.g., U.S. Pat. No. 7,674,739 B2; which is incorporated herein by reference. Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the conjunct polymer to be removed from the IL phase. See e.g., U.S. Pat. No. 7,727,925, which is incorporated herein by reference. The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727, which is incorporated herein by reference. Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740, which is incorporated herein by reference. The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771, which is incorporated herein by reference. Still another method involves adding a suitable substrate (e.g. pyridine) to the ionic liquid containing the conjunct polymer. After a period of time, an inert hydrocarbon would be added to wash away the liberated conjunct polymer. The ionic liquid precursor [butylpyridinium][Cl] would be added to the ionic liquid (e.g. [butylpyridinium][$Al_2Cl_7$]) containing the conjunct polymer followed by an inert hydrocarbon. After a given time of mixing, the hydrocarbon layer would be separated, resulting in a regenerated ionic liquid. See, e.g., U.S. Pat. No. 7,737,067, which is incorporated herein by reference. Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623, which is incorporated herein by reference. Ionic liquids can be regenerated by contacting with silane compounds (U.S. application Ser. No. 14/269,943), borane compounds (U.S. application Ser. No. 14/269,978), Brønsted acids, (U.S. application Ser. No. 14/229,329), or $C_1$ to $C_{10}$ Paraffins (U.S. application Ser. No. 14/229,403), each of which is incorporated herein by reference.

Fresh ionic liquid 255 can be added to the recycled portion 235 of the ionic liquid catalyst 230 from the gravity settler 220 and/or regenerated ionic liquid catalyst 250 to form ionic liquid catalyst stream 205.

Small amounts of ionic liquid catalyst may remain in the alkylated products

The alkylated products 225 are sent to ionic liquid removal zone 260. The ionic liquid removal zone 260 can be an adsorber or an extraction unit. The adsorber can include an ion exchange resin in a packed bed. The extraction unit can be a countercurrent liquid-liquid extraction unit, for example. The extraction unit can utilize any polar solvent. Suitable polar solvents include, but are not limited to, water, alcohols, such as methanol, ethanol, isopropyl alcohol and the like, and ketones, such as acetone, esters, like methyl acetate or ethyl acetate, or combinations thereof. Water is particularly suitable because later separation includes water removal for water that enters with the aromatic compound.

The effluent 265 from the ionic liquid removal zone 260 is sent to a fractionation zone for separation.

The effluent 265 is sent to benzene distillation column 270 to be separated into benzene overhead stream 275 and the bottoms stream 280. The benzene overhead stream 270 can be combined with a fresh aromatic stream 285 to form aromatic stream 200. The bottoms stream 280 is sent to the paraffin distillation column 290 where it is separated into the paraffin overhead stream 295 and the bottoms stream 300. The bottoms stream 300 is sent to the linear alkylbenzene distillation column 305 where it is separated into monoalkylated aromatic stream and dialkylated and higher aromatic stream 315.

In further detail for purposes of illustration, benzene distillation is generally conducted with a bottoms temperature of less than about 300° C., preferably less than about 275° C., usually between about 230° C. and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction. Water is removed in the benzene distillation, and the benzene is dry.

Each column used for benzene distillation may contain any convenient packing or distillation trays, but most often trays such as sieve and bubble trays, are used. Often the assembly provides at least about 5 theoretical plates, for example, 6 to 70, or 20 to 50. The reflux ratio is often in the range of about 2:1 to 1:10, or about 1.5:1 to 1:5. The bottoms stream from the benzene distillation generally contains less than about 1000 ppmw, or less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., or less than about 275° C., usually between about 250° C. and 275° C., and at a pressure at which overhead is provided of between about 5 and 110 kPa absolute, or between about 10 and 50 kPa absolute. The column may contain any convenient packing or distillation trays, but most often sieve trays are used. Often the paraffins distillation assembly provides at least about 5 theoretical plates, or about 7 to about 20. The reflux ratio is often in the range of about 3:1 to 1:10, or about 1:1 to 1:3. The bottoms stream from the paraffins distillation generally contains less than about 5000, or less than about 500, parts by million by weight (ppmw) paraffins and less than about 10, often less than about 1, ppmw benzene. The paraffins distillation may occur in a single column, or two or more distinct columns may be used.

The heavy alkylate distillation is generally conducted with a bottoms temperature of less than about 300° C., or less than about 275° C., usually between about 250° C. and 275° C., and at a pressure of between about 0.5 and 30 kPa absolute, or between about 1 and 5 kPa absolute. The column may contain any convenient packing or distillation trays, but most often structured packing is used. Often the heavy alkylate distillation assembly provides at least about 5 theoretical plates, for example 10 to 30, or 10 to 20. The reflux ratio is often in the range of about 2:1 to 1:5, or about 0.2:1 to 1:1. The overhead from the heavy alkylate distillation generally contains less than about 1000, or less than about 100 ppmw, and sometimes less than about 50 ppmw, total heavies.

The refining system may contain additional distillation zones, e.g., to recover additional alkylbenzene from heavies.

It will be appreciated by one skilled in the art that various features of the above described process, such as pumps, instrumentation, heat-exchange and recovery units, condensers, compressors, flash drums, feed tanks, and other ancillary or miscellaneous process equipment that are traditionally used in commercial embodiments of hydrocarbon conversion processes have not been described or illustrated. It will be understood that such accompanying equipment may be utilized in commercial embodiments of the flow schemes as described herein. Such ancillary or miscellaneous process equipment can be obtained and designed by one skilled in the art without undue experimentation.

By the term "about," we mean within 10% of the value, or within 5%, or within 1%.

EXAMPLE

A stream containing 10.7 wt. % dodecene-1 in octane was introduced into a stirred reactor containing benzene and 1-Butyl-3-methylimidazolium chloride-$AlCl_3$ ([BMIM]Cl) ionic liquid catalyst. The average molecular weight of the olefins was between 152 and 172. The ratio of ionic liquid catalyst to hydrocarbons was controlled between 0.5:1 and 2.0:1 (vol/vol). The benzene to olefin molar ratio was between 4:1 and 8:1. Under these conditions, formation of dialkylbenzene and dialkyltetralins was minimal The hydrocarbon and ionic liquid were easily separated by gravity in a settler. Under these conditions, separation was completed within 90 sec.

Preparative alkylation of benzene with 10.7 wt. % dodecene-1 in octane catalyzed by binary system [BMIM]Cl—$AlCl_3$ (1:1.5) at 40° C.

| Cycle | $\dfrac{C_6H_6}{C_{12}H_{24}}$ mol/mol | $\dfrac{IL + AlCl_3}{C_{12}H_{24}}$ wt/wt | Time, min | $C_{12}H_{24}$ Conversion % | ΣYield of LABs, % | Product distribution, %[a] | | | | | | | |
|---|---|---|---|---|---|---|---|---|---|---|---|---|---|
| | | | | | | 1 | 2 | 3 | 4 | 5 | 6 | 7 | 8 |
| 1 | 3.7 | 1.14 | 10 | 81.1 | 99.0 | 33.8 | 22.0 | 20.0 | 12.5 | 10.7 | traces | 0.9 | 0.1 |
| | | | 20 | 98.9 | 93.4 | 27.2 | 20.9 | 20.6 | 12.1 | 12.6 | traces | 3.9 | 2.7 |
| | | | 35 | 100 | 93.6 | 27.0 | 20.5 | 20.9 | 12.4 | 12.8 | traces | 3.7 | 2.7 |
| 2 | 3.7 | 1.14 | 10 | 71.5 | 95.8 | 27.5 | 20.4 | 20.6 | 12.4 | 12.5 | traces | 3.8 | 0.4 |
| | | | 21 | 99.9 | 95.7 | 27.3 | 20.5 | 20.5 | 12.4 | 12.7 | traces | 3.9 | 0.4 |
| | | | 34 | 100 | 93.4 | 27.2 | 20.9 | 20.6 | 12.1 | 12.6 | traces | 3.9 | 2.7 |
| 3 | 3.9 | 1.12 | 15 | 76.5 | 93.8 | 27.0 | 20.6 | 20.3 | 13.4 | 12.5 | traces | 3.1 | 3.1 |
| | | | 31 | 98.9 | 92.6 | 26.8 | 20.2 | 20.0 | 13.0 | 12.6 | traces | 4.3 | 3.1 |
| | | | 48 | 100 | 91.8 | 26.2 | 20.1 | 20.0 | 12.8 | 12.5 | traces | 5.1 | 3.1 |
| 4[b] | 4.3 | 1.22 | 10 | 100 | 95.8 | 30.1 | 20.6 | 20.0 | 12.6 | 12.5 | traces | 3.9 | 0.3 |
| | | | 29 | 100 | 95.7 | 27.2 | 20.4 | 20.6 | 12.6 | 12.1 | traces | 3.9 | 0.4 |
| 5 | 4.8 | 1.13 | 13 | 100 | 91.7 | 26.2 | 20.3 | 20.0 | 12.6 | 12.5 | traces | 5.1 | 3.0 |
| | | | 25 | 100 | 91.7 | 26.0 | 20.3 | 20.2 | 12.4 | 12.7 | traces | 5.1 | 3.0 |

Notes:
[a]1—2-phenyldodecane, 2—3-phenyldodecane, 3—4-phenyldodecane, 4—5-phenyldodecane, 5—6-phenyldodecane, 6—ΣNonlinear alkylbenzenes, 7—Lites (Σalkylbenzenes with M.w. 190 and 204), 8—Heavies (Σalkylbenzenes with M.w. 414 and more);
[b]catalyst was purified.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for making linear alkyl aromatics comprising:
dehydrogenating normal paraffins in a dehydrogenation zone to form a stream comprising $C_6$ to $C_{30}$ olefins;
selectively hydrogenating diolefins in the stream comprising olefins in a selective hydrogenation zone to form a stream comprising normal olefins;
adsorbing aromatics from the stream comprising normal olefins in an aromatics adsorption unit to form a stream comprising olefins having a lower aromatic content;
contacting an aromatic feed and the stream comprising olefins having the lower aromatic content in the presence of an ionic liquid catalyst in an alkylation reaction zone under alkylating conditions to form a product mixture comprising a mixture of alkylated aromatics comprising monoalkylated aromatics and dialkylated aromatics, the mixture of alkylated aromatics comprising greater than 90% linear alkylated aromatics, wherein a volume ratio of ionic liquid catalyst to hydrocarbon is in a range of 0.05:1 to 2.0:1, the hydrocarbon comprising the aromatic feed and the alkylating agent, and wherein a molar ratio of the aromatic feed to the olefin is in a range of 4:1 to 8:1; wherein the ionic liquid catalyst comprises at least one of 1-Butyl-3-methylimidazolium $AlCl_4$, 1-butyl-3-methylimidazolium $Al_2Cl_7$, 1-hexyl-3-methylimidazolium $AlCl_4$, and 1-hexyl-3-methylimidazolium $Al_2Cl_7$; and wherein a ratio of monoalkylated benzene to total alkylated product is greater than 0.95;
separating the ionic liquid catalyst from the product mixture by gravity into an ionic liquid catalyst stream and a product mixture stream;
removing any retained ionic liquid catalyst from the product mixture stream by adsorption or extraction; and
separating the product mixture stream into a stream comprising the monoalkylated aromatics and a stream comprising the dialkylated aromatics.

2. The process of claim 1 wherein the aromatic feed comprises benzene.

3. The process of claim 1 wherein the volume ratio of the ionic liquid catalyst to the hydrocarbon is in the range of 1:1 to 1.5:1.

4. The process of claim 1 wherein the aromatic feed comprises benzene, the olefin comprises $C_9$ to $C_{14}$ olefins, the mixture of alkylated aromatics comprises alkylated benzene, and wherein a selectivity for linear alkylated benzene is greater than 96%.

5. The process of claim 1 wherein the alkylating conditions include a temperature of from about 0° C. to about 80° C., and a pressure of from about 0.1 MPa to about 5 MPa.

6. The process of claim 1 further comprising regenerating the ionic liquid catalyst.

7. The process of claim 1 wherein removing any retained ionic liquid catalyst from the product mixture stream by adsorption or extraction comprises removing any retained ionic liquid catalyst from the product mixture stream comprising by extraction using a polar solvent.

8. The process of claim 1 wherein the product mixture further comprises unreacted aromatic feed, and unreacted normal paraffins, and wherein separating the product mixture stream into the stream comprising the monoalkylated aromatics and the stream comprising the dialkylated aromatics comprises separating the product mixture stream into a stream comprising the unreacted aromatic feed, a stream comprising the unreacted paraffins, the stream comprising the monoalkylated aromatics, and the stream comprising the dialkylated aromatics.

9. The process of claim 8 further comprising at least one of:
recycling the unreacted aromatic feed stream to the alkylation reaction zone; and
recycling the unreacted paraffins stream to the dehydrogenation zone.

10. The process of claim 1 wherein contacting the aromatic feed and the stream comprising olefins having the lower aromatic content in the presence of the ionic liquid catalyst in the alkylation reaction zone comprises contacting the aromatic feed and the stream comprising olefins having the lower aromatic content in the presence of the ionic liquid catalyst and an acid or acid precursor in the alkylation reaction zone.

11. An alkylation process comprising:
contacting benzene and an alkylating agent comprising an olefin $C_6$ to $C_{30}$ olefins in the presence of a halometallate ionic liquid catalyst in an alkylation reaction zone under alkylating conditions to form a product mixture comprising a mixture of alkylated benzene, unreacted benzene, and unreacted alkylating agent, the mixture of alkylated benzene comprising greater than 90% linear alkylated benzene, wherein the ionic liquid catalyst comprises at least one of 1-Butyl-3-methylimidazolium $AlCl_4$, 1-butyl-3-methylimidazolium $Al_2Cl_7$, 1-hexyl-3-methylimidazolium $AlCl_4$, and 1-hexyl-3-methylimidazolium $Al_2Cl_7$;
wherein a volume ratio of ionic liquid catalyst to hydrocarbon is in a range of 0.05:1 to 2.0:1, the hydrocarbon comprising the benzene and the alkylating agent;
wherein a molar ratio of the benzene to the olefin is in a range of 4:1 to 8:1;
wherein a ratio of monoalkylated benzene to total alkylated product is greater than 0.95;
separating the halometallate ionic liquid catalyst from the product mixture by gravity into an ionic liquid catalyst stream and a stream of the product mixture;
removing any retained ionic liquid catalyst from the product mixture stream by adsorption or extraction;
separating the product mixture stream into a stream comprising the monoalkylated benzene, a stream comprising the dialkylated benzene, a stream comprising the unreacted benzene, and a stream comprising the unreacted alkylating agent;
recycling the unreacted benzene stream to the alkylation reaction zone; and
recycling the unreacted alkylating agent stream to a dehydrogenation zone.

12. The process of claim 11 wherein the volume ratio of the ionic liquid catalyst to the hydrocarbon is in the range of 1:1 to 1.5:1.

13. The process of claim 12 wherein removing any retained ionic liquid catalyst from the product mixture stream comprises removing any retained ionic liquid catalyst from the product mixture stream by extraction using a polar solvent.

* * * * *